(12) United States Patent
Bories et al.

(10) Patent No.: US 9,547,066 B2
(45) Date of Patent: Jan. 17, 2017

(54) CALIBRATION OF AN ANTENNA ARRAY

(71) Applicant: Commissariat a l'Energie Atomique et aux Energies Alternatives, Paris (FR)

(72) Inventors: Serge Bories, Eybens (FR); Lama Ghattas, Grenoble (FR); Dominique Picard, Bonnelles (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 129 days.

(21) Appl. No.: 14/525,423

(22) Filed: Oct. 28, 2014

(65) Prior Publication Data

US 2015/0115978 A1    Apr. 30, 2015

(51) Int. Cl.
| | | |
|---|---|---|
| *H01Q 15/08* | (2006.01) | |
| *G01R 35/00* | (2006.01) | |
| *H01Q 1/42* | (2006.01) | |
| *G01N 21/63* | (2006.01) | |
| *G01S 7/40* | (2006.01) | |
| *H01Q 3/26* | (2006.01) | |
| *H01Q 5/22* | (2015.01) | |

(52) U.S. Cl.
CPC ............. *G01R 35/00* (2013.01); *G01N 21/63* (2013.01); *G01S 7/4021* (2013.01); *H01Q 1/42* (2013.01); *H01Q 3/267* (2013.01); *H01Q 5/22* (2015.01); *H01Q 15/08* (2013.01)

(58) Field of Classification Search
CPC .......... H01Q 15/08; H01Q 3/267; H01Q 1/42; H01Q 5/22; G01S 7/4021; G01N 21/63; G01R 35/00

USPC .......................................... 324/601
See application file for complete search history.

(56) References Cited

U.S. PATENT DOCUMENTS

| | | | |
|---|---|---|---|
| 4,954,834 A | | 9/1990 | Buck |
| 5,066,921 A | * | 11/1991 | Rope ...................... B82Y 15/00 |
| | | | 324/639 |
| 5,182,564 A | * | 1/1993 | Burkett ................... F41G 7/008 |
| | | | 342/53 |
| 5,371,505 A | * | 12/1994 | Michaels ................. H01Q 1/42 |
| | | | 324/639 |
| 5,384,458 A | | 1/1995 | Hilliard et al. |
| 5,963,034 A | | 10/1999 | Mahapatra et al. |
| 5,991,036 A | * | 11/1999 | Frankel .................. G01V 8/005 |
| | | | 324/244.1 |
| 6,127,966 A | * | 10/2000 | Erhage .................. G01S 7/4026 |
| | | | 342/165 |
| 6,708,020 B1 | * | 3/2004 | Hiramatsu ................ H04L 1/24 |
| | | | 342/173 |
| 6,771,216 B2 | | 8/2004 | Patel et al. |
| 7,911,376 B2 | | 3/2011 | Hardacker et al. |
| 2012/0038539 A1 | | 2/2012 | Chang |

OTHER PUBLICATIONS

Hamidreza Memarzadeh-Tehran, et al., "Optically Modulated Probe for Precision Near-Field Measurements", IEEE Transactions on Instrumentation and Measurement, vol. 59, No. 10, Oct. 2010.
Search Report issued on Jul. 23, 2014 in French Patent Appln 13/60536.

* cited by examiner

*Primary Examiner* — Son Le
*Assistant Examiner* — Akm Zakaria
(74) *Attorney, Agent, or Firm* — Moreno IP Law LLC

(57) ABSTRACT

An antenna system including at least one antenna connected to a captured signal processing receiver, an antenna protection radome; and a plurality of electro-optical probes distributed on or inside of the radome.

9 Claims, 2 Drawing Sheets

CALIBRATION OF AN ANTENNA ARRAY

BACKGROUND

The present disclosure generally relates to antennas and, more specifically, to the calibration of an antenna or of an antenna array to take into account disturbances of the radiation due to the immediate environment of the antenna(s), and to the reliability of such a calibration.

DISCUSSION OF THE RELATED ART

An antenna array, in particular in goniometry, scan radar, tracking radar, radio-guiding, beam monitoring or other applications, needs to be calibrated to provide reliable data. However, such antenna arrays are particularly sensitive to their environment and, in particular, to modifications at the level of the device carrying the antenna array (generally called carrier). It for example is a building, a vehicle, and more generally any device capable of being equipped with an antenna or with an antenna array.

Typically, knowing the nature of the carrier on which the antenna array is to be mounted, a laboratory calibration of the array is provided, either by emulating the immediate environment of the array during the calibration measurement in a controlled environment (for example, an anechoic room), or by simulating such disturbances originating from the immediate environment by digital calculations. The calibration generally comprises determining coefficients for correcting the response of the array (in amplitude and in phase) when the latter receives signals in a given direction, for example, the ratio of the voltage delivered by each channel to an incident field (effective height). The calibration is performed over the entire useful frequency band.

The disturbances which are desired to be corrected are those associated with the antenna array carrier (typically, another electronic device, another antenna, etc.). In most applications, the calibration of the far-field array response can be deduced from near-field measurements via a near field/far field transformation. The calibration is thus generally performed in a controlled environment (anechoic room) on one or a plurality of set configurations of the immediate environment of the array.

Now, the tendency to decrease the bulk of systems leads to placing the antennas closer to the disturbing elements (for example, by decreasing the height of the antenna mast). This generates a need for a new calibration of the antenna array as soon as its immediate environment is modified. Typically when new equipment is installed on the device carrying the antenna array, a new calibration is required. Now, this requires simulating again the immediate environment of the antenna array or carrying out a new calibration campaign to update the tables providing the array response coefficients.

Such a calibration is complicated to implement, in particular due to the fact that antenna arrays, once in use, are not always easily accessible. Further, the calibration performed by simulation is less accurate and less reliable than a measurement campaign.

U.S. Pat. No. 5,384,458 describes an electromagnetic sensor for a missile and provides including, within the missile head (within the volume defined by the missile case and not at the surface of this case), a plurality of photon sensors.

SUMMARY

An embodiment of the present invention aims at overcoming all or part of the disadvantages of antenna or antenna array calibration systems.

Another embodiment of the present disclosure aims at providing a calibration system which is non-invasive, that is, which adds no disturbance to those due to the immediate environment of the antenna(s).

Another embodiment aims at providing a calibration method which overcomes all or part of the disadvantages of known solutions.

Another embodiment aims at providing a solution which is particularly easy to implement and adapted to different types of antennas or of antenna arrays.

An embodiment aims at providing a near-real-time field calibration.

Thus, an embodiment provides an antenna system comprising:
at least one antenna connected to a captured signal processing receiver;
an antenna protection radome; and
a plurality of electro-optical probes distributed at the surface or across the thickness of the radome.

According to an embodiment, the system further comprises a laser intended to excite, through optical fibers, electro-optical probes.

According to an embodiment, the system further comprises a device for transmitting a radio signal.

According to an embodiment, the electro-optical probes are distributed at regular angular positions.

According to an embodiment, the receiver calculates and stores correction coefficients for the signals delivered by the antenna(s).

According to an embodiment, the system comprises a plurality of antennas forming an antenna array.

According to an embodiment, said receiver interprets in a calibration phase, the signals retromodulated by the probes to determine correction coefficients for signals received by the antenna(s).

An embodiment provides a method of calibrating a receiver of the above-described system, comprising the steps of:
a. transmitting a radio signal at a first frequency;
b. transmitting an optical signal intended to excite the probes at a second frequency;
c. analyzing the signals received from the antenna(s);
d. determining correction coefficients to be applied to the signals delivered by the antenna(s).

According to an embodiment, the method further comprises a step d) where correction coefficients to be applied to the signals delivered by the antenna(s) are determined.

According to an embodiment, the analysis of step c is performed at the first frequency and at frequencies corresponding to this first frequency, respectively decreased and increased by the second frequency.

According to an embodiment, steps b and c are successively carried out for each of said probes.

According to an embodiment, steps a to d are repeated for a plurality of values of the first frequency.

BRIEF DESCRIPTION OF THE DRAWINGS

The foregoing and other features and advantages will be discussed in detail in the following non-limiting description of specific embodiments in connection with the accompanying drawings, in which.

DETAILED DESCRIPTION

Figure 1:
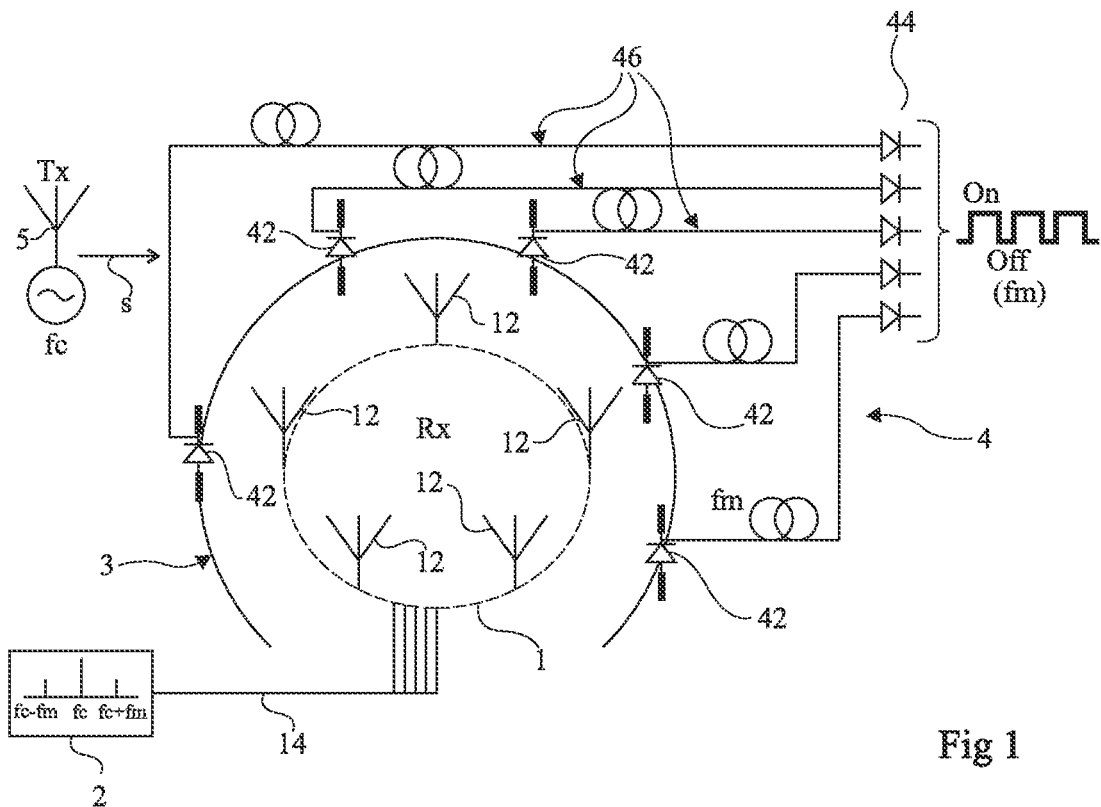
FIG. 1 is a simplified representation of an embodiment of an antenna array system.

The same elements have been designated with the same reference numerals in the different drawings. For clarity, only those steps and elements which are useful to the understanding of the embodiments to be described have been shown and will be detailed. In particular, the processing of the signals captured by the antennas in operation has not been detailed, the described calibration embodiments being compatible with usual applications and usual processing of such signals. Further, the implementation of the actual antenna or of the antenna array has not been detailed either, the described embodiments being here again compatible with usual implementations.

The present disclosure will refer hereafter to an embodiment applied to an antenna array used as a goniometer to determine the bearing of a signal. It should however be noted that the embodiments which will be described more generally apply to any antenna or any antenna array for which an in-situ calibration is desired to be performed.

As previously indicated, antenna arrays are conventionally calibrated by simulating the immediate environment or by measuring in a controlled environment the behavior of the antenna array on the carrier device. As an example, for an antenna array carried by a vehicle, the position on the vehicle of new electronic equipment or of a metal element generates disturbances in the antenna array and requires a new calibration. Conventionally, when it is known that the environment will be disturbed by the addition of a new device, the antenna array is calibrated again according to its carrier.

Such calibration systems have the disadvantage of not taking into account modifications of the immediate environment when the antenna array is in a functional environment.

It is provided to perform an in-situ calibration by permanently installing, in little intrusive fashion, a measurement device around the antenna array. A difficulty of calibrating the antenna array in its functional environment is that the measurement device should not impact the operation of the antenna, that is, it should not disturb its operation outside of the calibration phase.

FIG. 1 is a simplified representation of an antenna array equipped with an embodiment of a calibration system.

The shown example assumes an array 1 of antennas 12. The number of antennas varies according to applications and may be in the range from one antenna to several tens of antennas. Antennas are connected (connections 14) to an electronic signal processing system 2.

Mechanically, antenna array 1 is protected from the outside by means of a radome 3 which forms a case around the antenna array, protecting it from outer elements. The material forming the radome is selected not to introduce disturbances in the antenna array.

The above-described elements form the usual elements of an antenna array.

The radome may be provided with an assembly 4 of calibration probes 42. A specificity of such probes is that they are electro-optical probes each formed of a photodiode (for example, a non-biased wide-band photodiode) having its electrodes connected to conductive strands, each forming an antenna. Probes 42 are individually connected to one or a plurality of optical transmission devices 44 by a network of optical fibers 46. Transmission device 44 is in practice a laser transmitting an optical signal at a frequency fm. This signal is used to modulate a non-modulated radio signal s transmitted at a frequency fc. Signal s is generated by a transmit antenna 5 dedicated to the calibration. Each electro-optical probe 42, excited at frequency fm (for example, having a selected value ranging from a few tens to a few hundreds of kHz) smaller than frequency fc (for example, having a selected value ranging from a few hundreds of MHz to a few hundreds of GHz), modulates the field back-scattered by the considered probe. Antennas 12 detect the result of this modulation. Accordingly, signal processing system 2 receives, for each antenna 12, a signal which exhibits a spectrum having a main stripe at frequency fc, surrounded with stripes representing the modulated signal, at frequencies fc−fm and fc+fm.

When a disturbing element enters the area close to an antenna 12, the signals at frequencies fc and fc+/−fm are altered as compared with the nominal configuration. They thus contain different data to be analyzed in the new context of antenna 12. The modification (in amplitude and in phase) of the signal at frequency fc provides information as to the presence of the disturbing element without enabling to deduce the impact on the array in a given angular direction. However, the analysis of the signal at fc+/−fm which originates from the considered probe contains the impact of the disturbing element on each antenna of the array and this, only in the probe direction (probe—considered antenna axis).

Figure 2A:
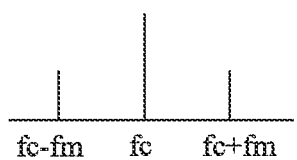
FIGS. 2A and 2B very schematically show examples of spectrums received by a receiver of the system during a calibration phase.
Figure 2B:
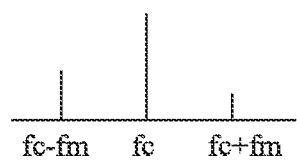

FIGS. 2A and 2B very schematically illustrate examples of spectrums of the received signal in the presence of a disturbance in a given direction relative to the antenna array. These drawings show two examples of spectrums analyzed by processing system 2, originating from two different antennas. This example is arbitrary and illustrates that a disturbing element in the near field of the antenna will cause a modification of the module and of the phase of the received signal, which differs for each of the antennas according to the angular position of the disturbing element. The analysis of the signals received in the calibration phase thus enables to identify the disturbing elements and to determine correction coefficients to be applied so that the receiver recovers a nominal operation.

The choice of electro-optical probes associated with the choice of conveying the modulation signal by means of optical fibers suppresses the metal elements disturbing the calibration system, which enables to leave it permanently, integrated to radome 3. In particular, the electric antennas connected to the radio frequency outputs of the electro-optical probes are selected to have a sufficiently small size (for example, smaller than λmin/2, where λmin represents the minimum operating wavelength of the antenna array) to avoid disturbing the near field when the system is being used. Such a small size is not disturbing for the actual calibration due to the proximity between the radome antennas and the antennas of the antenna array, so that the antenna array will be capable of receiving the modulation back-scattered by probes 42.

For example, article "Optically Modulated Probe for Precision Near-Field Measurements" by H. Memarzadeh-Tehran et al., published in IEEE Transactions on Instrumentation and Measurement, volume 59, No 10 in October 2010, may be used as a guideline.

The electro-optical probes are preferably all arranged at the external or internal surface of the radome or across the thickness thereof (embedded in the material forming the radome). This contributes to the reliability of the calibration.

Figure 3:
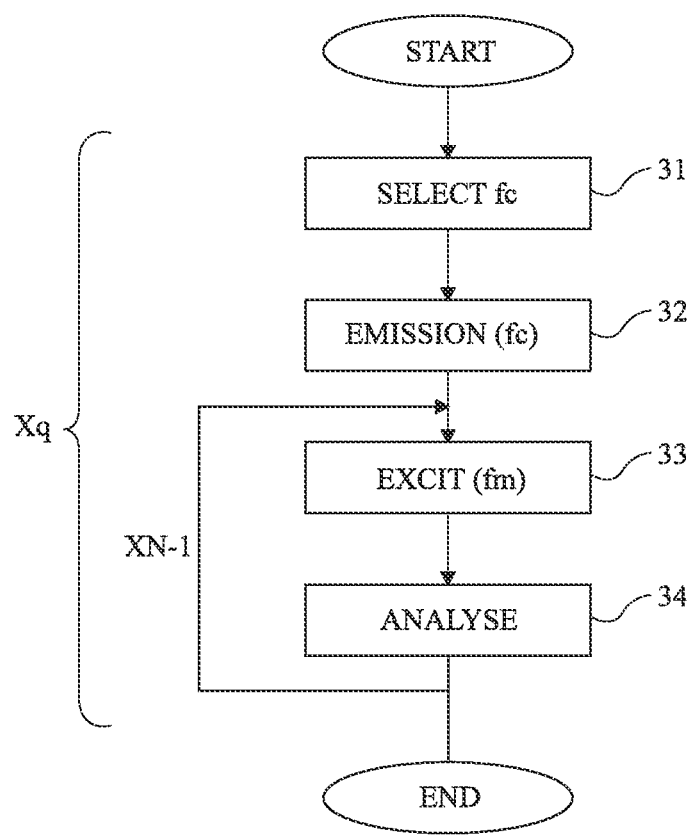
FIG. 3 very schematically illustrates, in the form of blocks, steps of a method of calibrating an antenna array in the system of FIG. 1.

FIG. 3 is a block diagram of an embodiment of a calibration method using the system of FIG. 1.

In a first step (block 31, SELECT fc), a central frequency fc to be transmitted by device 5 should be selected.

After this (block 32, TRANSMISSION (fc)), transmit antenna 5, dedicated to the calibration, transmits a radio signal at frequency fc.

Laser 44 sequentially excites (block 33, EXCIT fm) the N electro-optical probes 42 at frequency fm to ease the signal processing (steps 33 and 34 repeated N−1 times). As a variation, a simultaneous excitation of the N probes is also possible by assigning, to each probe, a coding of the modulated signal.

The signals received on the different antennas 12 are processed (block 34, ANALYZE) by receiver 2 to determine the possible disturbance of an element in the environment of the antenna array.

This operation is repeated q times for each probe 42, q representing the number of the calibration frequencies. The values of the correction coefficients (calibration tables) to be introduced in the antenna system can then be deduced.

An advantage of the described embodiments is that it is now possible to carry out phases of calibrating an antenna array while the latter is in its environment, the frequency of such calibration phases depending on the application. It may for example be chosen to carry out a calibration phase each time the carrier of the antenna array is modified by the adding of a new device. Periodical sampling phases may also be provided.

Another advantage of the described embodiments is that the calibration system does not disturb the actual operation of the antenna array and that it can thus remain in place. In particular, its integration in the radome, which is itself a non-disturbing element for the field, is particularly adapted, due to the proximity between the radome and the antenna array and due to the shape of the radome, which generally surrounds the array in all relevant directions for the reception.

Various embodiments have been described. Various alterations, modifications, and improvements will occur to those skilled in the art. In particular, the selection of the q excitation frequencies fc depends on the application, that is, on the operating frequency band of the antenna array. Modulation frequency fm is smaller than the smallest value of frequency fc, by a ratio of at least 10. Further, number N of probes to be angularly distributed around the radome also depends on the application and on the accuracy desired for the calibration. Further, the practical implementation of the described embodiments is within the abilities of those skilled in the art based on the functional indications given hereabove and by using techniques usual per se of signal interpretation for calibration purposes and the usual operation of electro-optical probes and antennas. Reference may for example be made to thesis "Radiogoniométrie: Modélisation-Algorithme-Performance" by Anne Ferréol.

The invention claimed is:

1. A method of calibrating a receiver of an antenna system comprising at least one antenna connected to the receiver, an antenna protection radome, and a plurality of electro-optical probes distributed on or inside of the radome, comprising the steps of:
   a. transmitting an unmodulated radio signal at a first frequency;
   b. transmitting an optical signal intended to excite the probes at a second frequency to modulate the radio signal;
   c. analyzing the signals received from the at least one antenna; and
   d. determining correction coefficients to be applied to the signals delivered by the at least one antenna,
   wherein steps a) to d) are repeated for a plurality of values of the first frequency.

2. The method of claim 1, wherein the analysis of step c is performed at the first frequency and at frequencies corresponding to this first frequency, respectively decreased and increased by the second frequency.

3. The method of claim 1, wherein steps b and c are successively carried out for each of said probes.

4. An antenna system comprising:
   at least one antenna connected to a captured signal processing receiver;
   an antenna protection radome; and
   a plurality of electro-optical probes distributed at the surface or within the thickness of the radome and configured to modulate, at a second frequency, an unmodulated radio signal incident on each of the electro-optical probes,
   wherein said receiver demodulates in a calibration phase, signals backscattered by the probes to determine correction coefficients for signals received by the at least one antenna.

5. The system of claim 4, further comprising a laser intended to excite, through optical fibers, electro-optical probes.

6. The system of claim 4, further comprising a device for transmitting a radio signal.

7. The system of claim 4, wherein the electro-optical probes are distributed at regular angular positions.

8. The system of claim 4, wherein the receiver calculates and stores correction coefficients for the signals delivered by the at least one antenna.

9. The system of claim 4, comprising a plurality of antennas forming an antenna array.

* * * * *